United States Patent [19]
Kronis et al.

[11] Patent Number: 5,382,658
[45] Date of Patent: Jan. 17, 1995

[54] STABILITY-ENHANCED VARIANTS OF PARATHYROID HORMONE

[75] Inventors: K. Anne Kronis, Toronto; Richard P. Bozzato, Etobicoke, both of Canada

[73] Assignees: Allelix Biopharmaceuticals Inc.; Glaxo Canada Inc., Mississauga, Canada

[21] Appl. No.: 863,014

[22] Filed: Apr. 3, 1992

[51] Int. Cl.$^6$ .................. C07K 3/00; A61K 37/02; A61K 37/00; A01N 37/18

[52] U.S. Cl. .................. 530/397; 530/324; 514/2; 514/8; 514/12

[58] Field of Search .................. 435/69.1, 69.4, 172.1, 435/172.2, 172.3, 6, 240.2, 320.1; 530/324, 350, 351, 387, 388, 397, 398, 399; 536/23.1-23.52; 514/2, 8, 12

[56] References Cited

U.S. PATENT DOCUMENTS

| | | | |
|---|---|---|---|
| 4,423,037 | 12/1983 | Rosenblatt et al. | 424/177 |
| 4,698,328 | 10/1987 | Neer et al. | 514/12 |
| 4,761,406 | 8/1988 | Flora et al. | 514/86 |
| 4,968,669 | 11/1990 | Rosenblatt et al. | 514/12 |

FOREIGN PATENT DOCUMENTS

| | | |
|---|---|---|
| 0293159 | 5/1988 | European Pat. Off. . |
| 0357391 | 8/1989 | European Pat. Off. . |
| 477885A2 | 1/1992 | European Pat. Off. . |
| 0561412A1 | 9/1993 | European Pat. Off. . |
| WO86/06097 | 10/1986 | WIPO . |
| 8800596A | 1/1988 | WIPO . |
| WO88/03165 | 5/1988 | WIPO . |
| WO90/10067 | 9/1990 | WIPO . |

OTHER PUBLICATIONS

Reppe et al, "Characterization of a K26Q Site-Directed Mutant Of Human Parathyroid Hormone Expressed In Yeast", *J. Biol. Chem.*, 266:14198-14201, (1991).

Rosenblatt et al., "Modification Of The Arginines In Parathyroid Hormone: Effect On Biological Activity," *Biochemistry*, 17:3188, (1978).

Rodan et al, "Factors Associated With Humoral Hypercalcemia Of Malignancy Stimulate Adenylate Cyclase In Osteoblastic Cells", *J. Clin. Invest.*, 72:1511-1515, (1983).

Rabbani et al, "Influence Of The Amino-Terminus On in Vitro and in Vitro Biological Activity Of Synthetic Parathyroid Hormone-Like Peptides Of Malignancy", 123:2709-2716, (1988).

Kimura et al, "Solution Synthesis Of [ASN$^{76}$]-Human Parathyroid Hormone (1-84)", *Biochem. Biophys. Res. Comm.*, 114:493-499 (1983).

Keutmann, "Current Research On Calcium Regulating Hormones", *University of Texas Press*, pp. 57-63, (1987).

Rosenblatt et al, "Chemical And Biological Properties Of Synthetic, Sulfur-free Analogues Of Parathyroid Hormone", *J.-Biol. Chem.*, 251:159-164, (1976).

Fairwell et al, "Total Solid-Phase Synthesis, Purification, and Characterization Of Human Parathyroid Hormone-(1-84)", *Biochemistry*, 22:2691, (1983).

Goud et al, "Solid-Phase Synthesis And Biologic Activity Of Human Parathyroid Hormone (1-84)", *J. Bone Min. Res.*, 6(8):781-789, (1991).

Wosnick et al, "Total Chemical Synthesis And Expression in *Escherichia coli* Of A aize Glutathione-Transferase (GST) Gene", *Gene*, 76:153-160, (1989).

Barnett et al, "Rapid Generation Of DNA Fragments By PCR Amplification Of Crude, Synthetic Oligonucleotides", *Nucl. Acids Res.*, 18(10):3094 (1990).

Hendy et al, "Nucleotide Sequence Of Cloned cDNAs Encoding Human Preproparathyroid Hormone", *Proc. Natl. Acad. Sci. U.S.A.*, 78:7365-7369, (1981).

(List continued on next page.)

Primary Examiner—Garnette D. Draper
Assistant Examiner—Gian P. Wang
Attorney, Agent, or Firm—Foley & Lardner

[57] ABSTRACT

Herein described are variants of parathyroid hormone that retain significant PTH activity and are substantially resistant to trypsin and trypsin-like enzymes. The variants are useful pharmaceutically, to treat bone disorders such as osteoporosis and in other therapeutic applications. Specific embodiments of the invention include [His$^{25}$]PTH and [His$^{25}$His$^{26}$Leu$^{27}$]PTH.

2 Claims, 2 Drawing Sheets

```
                                1                                                    10
                     SerValSerGluIleGlnLeuMetHisAsnLeuGlyLysHisLeuAsnSerMet
     ompA signal..TCTGTGAGTGAAATACAGCTTATGCATAACCTGGGAAAACATCTGAACTCGATG 20                        30                        40
     GluArgValGluTrpLeuArgLysLysLeuGlnAspValHisAsnPheValAlaLeuGlyAlaProLeuAla
     GAGAGAGTAGAATGGCTGCGTAAGAAGCTGCAGGATGTGCACAATTTTGTTGCCCTTGGAGCTCCTCTAGCT 50                        60
     ProArgAspAlaGlySerGlnArgProArgLysLysGluAspAsnValLeuValGluSerHisGluLysSer
     CCCAGAGATGCTGGTTCCCAGAGGCCCCGAAAAAAGGAAGACAATGTCTTGGTTGAGAGCCATGAAAAAAGT 70                        80
     LeuGlyGluAlaAspLysAlaAspValAsnValLeuThrLysAlaLysSerGln
     CTTGGAGAGGCAGACAAAGCTGATGTGAATGTATTAACTAAAGCTAAATCCCAG...cloning
                                                              site/stop
                                                              codons...
```

OTHER PUBLICATIONS

Kunkel T., "Rapid And Efficient Site-Specific Mutagenesis Without Phenotypic Selection", *Proc. Natl. Acad. Sci. USA*, 82:488–492, (1985).

Higuchi et al, "A General Method Of in vitro Preparation And Specific Mutagenesis Of DNA Fragments: Study Of Protein And DNA Interactions", *Nucl. Acids Res.*, 16:7351–7367, (1988).

Sarkar et al, "The Megaprimer Method Of Site-Directed Mutagenesis", *Biotechniques*, 8(1):404–407, (1990).

Rabbani et al, "Synthesis And Characterization Of Extended And Deleted Recombinant Analogues Of Parathyroid Hormone-(1-84): Correlation Of Peptide Structure With Function", *Biochemistry*, 29:10080–10089.

Laemmli, "Cleavage Of Structural Proteins During The Assembly Of The Head Of Bacteriophage T4", *Nature*, 227:680–685, (1970).

Schägger et al, "Tricine-Sodium Dodecyl Sulfate-Polacrylamide Gel Electrophoresis For The Separation Of Proteins In The Range From 1 to 100 kDa", *Analytical Biochemistry*, 166:368–379, (1987).

Reeve et al.; Anabolic Effect of Human Parathyroid Hormone Fragment on a Trabecular Bone in Involutional Osteoporosis: A Multicentre Trial; British Medical Journal (7 Jun. 1980) pp. 1340–1344.

Mosekilde et al.; The Anabolic Effects of Human Parathyroid Hormone (hPTH) on Rat Vertebral Body Mass Are also Reflected in the Quality of Bone, Assessed by Biomechanical Testing: A Comparison Study between hPTH-(1-34) and hPTH-(1-84); The Endocrine Society (vol. 129, No. 1).

FIG. 2

```
                         1                            10
             SerValSerGluIleGlnLeuMetHisAsnLeuGlyLysHisLeuAsnSerMet
ompA signal..TCTGTGAGTGAAATACAGCTTATGCATAACCTGGGAAAACATCTGAACTCGATG
                    20                    30                    40
GluArgValGluTrpLeuArgLysLysLeuGlnAspValHisAsnPheValAlaLeuGlyAlaAlaProLeuAla
GAGAGAGTAGAATGGCTGCGTAAGAAGCTGCAGGATGTGCACAATTTTGTGCCCTTGGAGCTCCTCTAGCT
                                         50                    60
ProArgAspAlaGlySerGlnArgProArgLysLysGluAspAsnValLeuValGluSerHisGluLysSer
CCCAGAGATGCTGGTTCCCAGAGGCCCCGAAAAAAGGAAGACAATGTCTTGGTTGAGAGCCATGAAAAAGT
                                               70                    80
LeuGlyGluAlaAspLysAlaAspValAlaAsnValLeuThrLysAlaLysSerGln
CTTGGAGAGGCAGACAAAGCTGATGTGAATGTATTAACTAAAGCTAAATCCCAG...cloning
                                                           site/stop
                                                           codons...
```

STABILITY-ENHANCED VARIANTS OF PARATHYROID HORMONE

FIELD OF THE INVENTION

This invention relates to parathyroid hormone. More particularly, the invention relates to variants of parathyroid hormone, to the production of such variants particularly via recombinant DNA technology and to the use of such variants as therapeutic agents, for example in the treatment of osteoporosis.

BACKGROUND TO THE INVENTION

Parathyroid hormone (PTH) is a secreted, protein product of mammalian parathyroid glands that regulates calcium homeostasis through its action on various tissues, including bone and vascular tissue. Research into the physiological role of PTH has identified clinically relevant effects on bone metabolism, there being some clinical evidence that PTH may be useful in the treatment of osteoporosis and related osteopenic afflictions. An effect on vascular tissue and on keratinocyte growth has also been noted.

To obtain PTH in the amounts required for clinical investigations and for commercial purposes, recombinant DNA-based techniques have been successfully applied in the production of such mammalian PTH species as human PTH, bovine PTH, porcine PTH and rat PTH, which in their mature form all contain 84 amino acids arranged in a species-specific sequence. An understanding of the structure of these proteins, and particularly human PTH and bovine PTH, has lead also to the discovery that PTH activity can be attributed to the first 34 N-terminal residues of the mature hormone. This has allowed for the production of biologically active PTH fragments using the solid phase technique of peptide synthesis, to meet PTH demand.

In the interest of furthering development of PTH as a pharmaceutical product, it would be desirable to provide stability-enhanced forms of PTH that are better suited for human administration. It is known from studies with serum-derived PTH samples, and from experience with recombinant PTH production, that the hormone is particularly vulnerable to protease digestion. PTH production in yeast, for example, has shown that PTH is degraded by the yeast-produced kex enzyme, which recognizes dibasic residues. When the lysine residue at position 26 of PTH is replaced with glutamine, however, proteolytic degradation of PTH by the yeast is reportedly reduced (see Reppe et al, J. Biol. Chem., 1991, 266:14198). Other studies targetting this general region of the PTH molecule have indicated that amino acid replacement can cause significant decline in PTH activity. Conversion of the lysine at position 27 for example, resulted in a marked decline in PTH activity (see Wingender et al, WO 90/10067) as did derivatization of the arginine residues at positions 25 and 20 (sse Rosenblatt et al, 1978, Biochemistry, 17:3188).

It is an object of the present invention to provide a novel variant of parathyroid hormone.

It is another object of the present invention to provide a parathyroid hormone variant that exhibits improved stability in the presence of proteolytic enzymes, especially trypsin and trypsin-like enzymes.

It is another object of the present invention to provide a parathyroid hormone variant that exhibits both improved stability in the presence of proteolytic enzymes and a bioactivity that is comparable to parathyroid hormone.

It is another object of the present invention to provide a pharmaceutical composition comprising a parathyroid hormone variant exhibiting improved stability and comparable activity, for use in therapeutic applications.

It is another object of the present invention to provide a process for producing a stability-enhanced variant of parathyroid hormone.

SUMMARY OF THE INVENTION

The present invention provides variants of parathyroid hormone that are altered structurally to confer enhanced stability in the presence of proteolytic enzymes such as trypsin and the so-called trypsin-like enzymes that cleave at internal arginine and lysine residues. Although numerous putative trypsin cleavage sites reside in native parathyroid hormone, it has surprisingly been found that substantial resistance to tryptic digestion is conferred when the hormone is altered at a single region constituted by residues $\text{Arg}^{25}\text{Lys}^{26}\text{Lys}^{27}$. It has further been found that variants having activity comparable to native parathyroid hormone are generated when replacement amino acids are selected appropriately. Thus, the PTH variants of the present invention are well suited for therapeutic applications and are better adapted to survive exposure particularly to trypsin and trypsin-like enzymes while in the peripheral circulation and also during their production, handling and storage.

According to one aspect of the present invention, there is provided a stability-enhanced variant of a parathyroid hormone compound harbouring the region $\text{Arg}^{25}\text{Lys}^{26}\text{Lys}^{27}$, in which said region is replaced in said variant by an amino acid sequence selected from:
 (a) $X^{25}\text{Lys}^{26}\text{Lys}^{27}$;
 (b) $\text{Arg}^{25}Y^{26}Z^{27}$
 (c) $X^{25}Y^{26}\text{Lys}^{27}$;
 (d) $X^{25}\text{Lys}^{26}Z^{27}$; and
 (e) $X^{25}Y^{26}Z^{27}$ wherein X, Y and Z are independently selected trypsin-insensitive amino acids i.e. amino acids other than lysine and arginine.

In a preferred embodiment of the invention, the replacement amino acids X, Y and Z are selected to yield variants of human PTH that in addition to exhibiting enhanced stability in the presence of trypsin, also exhibit an activity comparable to native human PTH. In specific embodiments of the invention, the replacement amino acids are selected from among the genetically encoded amino acids, to permit production of the variants via recombinant DNA-based techniques.

According to another aspect of the present invention, there is provided a pharmaceutical composition, comprising a therapeutically effective amount of a parathyroid hormone variant of the present invention and a pharmaceutically acceptable carrier.

According to another aspect of the present invention, there is provided a method for treating a mammal, which comprises the step of administering to a mammal in need thereof a pharmaceutical composition comprising a therapeutically effective amount of a parathyroid hormone variant of the present invention and a pharmaceutically acceptable carrier.

According to another aspect of the present invention, there is provided a process for producing a parathyroid hormone variant that exhibits enhanced stability in the presence of trypsin, which comprises the step of culturing a cellular host having incorporated expressibly therein a DNA molecule which codes for a PTH variant of the invention, in which each of the replacement amino acids is a genetically encoded amino acid.

The invention and its preferred embodiments are now described in greater detail with reference to the accompanying drawings, in which:

BRIEF REFERENCE TO THE DRAWINGS

FIG. 1 illustrates a recombinant DNA plasmid harbouring human PTH-encoding DNA, for expression in an *E. coli* host; and FIG. 2 illustrates the sequence of the human PTH-encoding DNA (SEQ ID NO:1) incorporated on the plasmid of FIG. 1, and provides the sequence of human PTH (SEQ ID NO:2) with the $Arg^{25}Lys^{26}Lys^{27}$ region identified by boxing.

DETAILED DESCRIPTION OF THE INVENTION AND PREFERRED EMBODIMENTS

Figure 1:
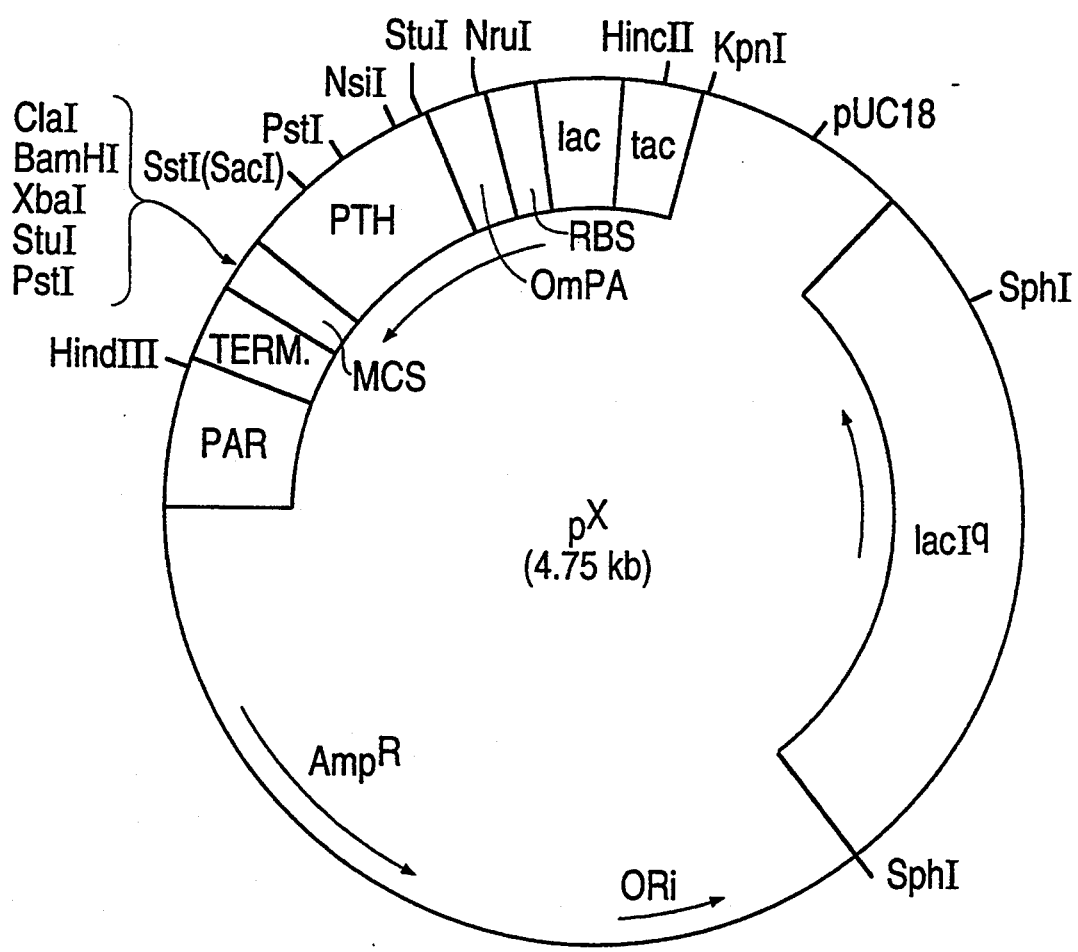

The invention relates to parathyroid hormone variants that exhibit improved stability in the presence of trypsin and, in accordance with a preferred aspect of the invention, also exhibit activity at least similar to native PTH. In the present specification, PTH activity is defined in the context of the osteosarcoma-based adenylate cyclase assay employed conventionally in the art. Briefly, this assay provides an in vitro determination of the extent to which PTH stimulates adenylate cyclase activity in rat osteosarcoma cells of the 'UMR' lineage, and thus provides an indication of PTH effects on bone tissue in vivo. Protocols for conducting the assay have been described by Rodan et al, 1983, J. Clin. Invest., 72:1511 (in which the osteosaracoma cells of the ROS lineage are employed) and by Rabbani et al, 1988, Endocrinol., 123:2709 (which employs the line UMR-106). PTH variants that exhibit, in the UMR-based assay, an $EC_{50}$ of at least 1,000 nM i.e. 1,000 nM or lower, are herein characterized as having activity "similar" to native PTH; a variant having an $EC_{50}$ of 100 nM or lower is characterized as having activity "substantially similar" to native PTH; and a variant having an $EC_{50}$ of 10 nM and lower is characterized as having an activity that is "comparable" to native PTH. The term $EC_{50}$ refers to the concentration of PTH or variant effective for half-maximal stimulation of adenylate cyclase activity.

PTH variants having an "improved stability in the presence of trypsin" are degraded by trypsin at a rate that is slower than a similarly treated native PTH control. An assay suitable for identifying a reduced tryptic digestion rate entails a two step procedure, in which a PTH variant and a native PTH control are separately incubated with trypsin for a defined period, and are then assayed for activity in the osteosarcoma-based assay just described. Protocols suitable for assaying trypsin sensitivity are described in the literature and are outlined in the examples herein. In this assay, variants of human PTH, for example, will exhibit an activity that is at least greater than a similarly treated native human PTH control. In a quantitative context, the PTH variants may be characterized as having an improved stability in the presence of trypsin if the variant exhibits an $EC_{50}$ as determined in the UMR-based adenylate cyclase assay that is at least lower than a similarly treated native PTH counterpart. Under conditions of the assay exemplified herein, for instance, native human PTH exhibits an $EC_{50}$ of about 12 nM following trypsin incubation. "Stability improved" human PTH variants are accordingly characterized by an $EC_{50}$ of lower than 12 nM, when assayed under these particular conditions.

In the present specification, amino acids are assigned numerals to identify their location relative to the N-terminal amino acid of mature PTH. For consistency and as is conventional in the art, amino acids are assigned the same positional number when present in the context of N-terminally truncated or extended forms of PTH.

In accordance with the present invention, PTH variants exhibiting improved stability in the presence of trypsin are obtained when the $Arg^{25}Lys^{26}Lys^{27}$ region of PTH is replaced with an amino acid sequence selected from:

(a) $X^{25}Lys^{26}Lys^{27}$;
(b) $Arg^{25}Y^{26}Z^{27}$;
(c) $X^{25}Y^{26}Lys^{27}$;
(d) $X^{25}Lys^{26}Z^{27}$; and
(e) $X^{25}Y^{26}Z^{27}$ wherein X, Y and Z are independently selected, trypsin-insensitive amino acids, i.e. amino acids other than arginine and lysine.

It has surprisingly been found that measurably improved stability in the presence of trypsin is realized when the $Arg^{25}Lys^{26}Lys^{27}$ region is altered by replacement merely of the $Arg^{25}$ residue. Thus, according to one embodiment of the present invention, there is provided a PTH variant having improved stability in the presence of trypsin, in which $Arg^{25}$ is replaced by an amino acid other than arginine and lysine.

According to another embodiment of the present invention, PTH variants exhibiting improved stability in the presence of trypsin are obtained by replacing both $Arg^{25}$ and $Lys^{26}$ with independently selected amino acids other than arginine and lysine.

According to another embodiment of the present invention, PTH variants exhibiting improved stability in the presence of trypsin are obtained by replacing both the $Arg^{25}$ and $Lys^{27}$ with independently selected amino acids other than arginine and lysine.

According to another embodiment of the present invention, PTH variants exhibiting improved stability in the presence of trypsin are obtained by replacing both the $Lys^{26}$ and $Lys^{27}$ with independently selected amino acids other than arginine and lysine.

PTH variants in which the entire $Arg^{25}Lys^{26}Lys^{27}$ region is replaced have been found to exhibit substantial resistance to tryptic digestion. According to a preferred embodiment of the present invention therefore, the PTH variants of the present invention are obtained by replacing each of the amino acids $Arg^{25}Lys^{26}Lys^{27}$ with an independently selected amino acid other than arginine and lysine.

The replacement amino acids X, Y and Z in the above formulae are trypsin-insensitive amino acids and may be chosen from among the various synthetic amino acids and the naturally occurring amino acids other than L-arginine and L-lysine. In a preferred aspect of the present invention, the replacement amino acids X, Y and Z are selected with a view to generating variants that exhibit activity comparable to native PTH. For this purpose, the replacement amino acids are selected from among those amino acids which preserve the same configuration in this region of the PTH molecule. More particularly, the replacement amino acids are most desirably selected from among those amino acids having either neutral or positively charged amino acid sidechains. Useful amino acid replacements having neutral side chains include glycine, alanine, valine, leucine, isoleucine, serine, threonine, asparagine, glutamine, phenylalanine, cysteine, tryptophan, tyrosine, methionine, proline, as well as the synthetic analogues thereof, such as norleucine, norvaline, cyclohexylalanine, etc. Amino acids having positively charged side chains include histidine and synthetic histidine analogues, such as D-histidine, 1-methyl-L-histidine, 3-methyl-L-histidine, N-imidazole-benzyloxycarbonyl (Z)-L-histidine and N-imidazole-benzyl-L-histidine.

In a particularly preferred aspect of the present invention, the replacement amino acids are selected from among the group of genetically encoded amino acids, in order to obtain PTH variants that can be produced by application of established, recombinant DNA-based techniques of protein production. In this respect, the replacement amino acids may be selected from among the group consisting of alanine, valine, leucine, isoleucine, phenylalanine, tyrosine, tryptophan, serine, threonine, asparagine, glutamine, histidine and proline. In a preferred embodiment of the invention, the replacement amino acids are selected from alanine, valine, leucine, isoleucine, histidine, glutamine, asparagine and proline. According to specific embodiments of the present invention, $X^{25}$ and $Y^{27}$ are preferably histidine and $Z^{27}$ is preferably leucine.

The amino acid replacements herein identified may be introduced into various forms of PTH, i.e. into different PTH "backgrounds", that in their native state contain the $Arg^{25}Lys^{26}Lys^{27}$ sequence. The replacement amino acids may be introduced for example into mature forms of vertebrate PTH, including chicken PTH, as well as mammalian PTH forms including porcine PTH, rat PTH, bovine PTH and also human PTH. The term "human PTH" refers to the mature form of the hormone, which consists of 84 amino acids arranged in the sequence reported by Kimura et al, 1983, Biochem. Biophys. Res. Comm., 114(2):493. The terms "human PTH" and "hPTH" are used interchangeably herein. The terms "bovine PTH", "rat PTH" and "porcine PTH" refer also to the mature form of the hormone, each of which consists of 84 amino acids arranged in the sequences reported by Keutmann et al in Current Research on Calcium Regulating Hormones, Cooper, C. W.(Ed.), 1987, University of Texas Press, Austin, pp.57-63.

The replacement amino acids may also be incorporated into biologically active fragments of mature PTH that contain the $Arg^{25}Lys^{26}Lys^{27}$ sequence. "Biologically active fragments" of PTH consist of at least the first 27 N-terminal residues of a mature PTH species, and most usually consist of amino acid residues 1-34. Thus, for example, the amino acid replacements herein described can be introduced for example into human PTH(1-34) and bovine PTH(1-34), as well as C-terminally extended fragments such as PTH(1-37) and PTH(1-38).

The amino acid replacements herein described can also be incorporated to improve the tryptic stability of PTH analogues and fragments thereof. The term "PTH analogue" is used herein with reference to $Arg^{25}Lys^{26}Lys^{27}$-containing forms of PTH having an altered amino acid sequence, such as an amino acid substitution at a site other than the $Arg^{25}Lys^{26}Lys^{27}$ region. Such PTH analogues and fragments thereof include those having substitutions for example at one or both of positions 8 and 18 whereby resident methionines are replaced by a hydrophobic amino acid such as norleucine or leucine (see copending U.S. Ser. No. 806,271 and see Rosenblatt et al, J. Biol. Chem., 1976, 251(1):159); analogues having a substitution at position 12 whereby the resident glycine is replaced by alanine, D-alanine, isobutyric acid, proline, tryptophan or asparagine (see Wingender et al, WO90/10067, and Rosenblatt et al U.S. pat. No. 4,968,669); analogues having a substitution at position 23 whereby the resident tryptophan is replaced by leucine, N-methyl-phenylalanine or D-tryptophan (see Merck & Co., EP 293,159); analogues having a substitution at position 32 whereby the resident histidine is replaced by arginine, leucine, lysine or serine (see Wingender et al, supra); and analogues having a substitution at position 34 whereby the resident phenylalanine is replaced by tyrosine.

The replacement amino acids can also be incorporated into N-terminally truncated versions of mature PTH and fragments, and analogues thereof, which contain the $Arg^{25}Lys^{26}Lys^{27}$ region. These forms of PTH have been described as antagonists of PTH action, and typically lack from 3 to 7N-terminal residues (see U.S. Pat. No. 4,423,037).

The term "PTH compound" as used herein thus embraces $Arg^{25}Lys^{26}Lys^{27}$-containing forms of PTH, including native PTH forms, N- and C-terminally truncated forms thereof, and analogues of these native and truncated forms.

In a preferred embodiment of the present invention, the replacement amino acids herein described are incorporated into human PTH, to yield human PTH variants that in addition to exhibiting improved stability in the presence of trypsin also exhibit activity comparable to native PTH. According to specific embodiments of the invention, such human PTH variants include:

(a) those in which the $Arg^{25}$ residue alone is replaced by a genetically encoded amino acid selected from histidine, tyrosine, tryptophan, glutamine, asparagine, alanine, phenylalanine, leucine and isoleucine. Specific compounds of the present invention include [His$^{25}$]hPTH, [Gln$^{25}$]hPTH, [Asn$^{25}$]hPTH, [Phe$^{25}$]hPTH, [TrP$^{25}$]hPTH. [Tyr$^{25}$]hPTH, [Ala$^{25}$]hPTH, [Val$^{25}$]hPTH, [Ile$^{25}$]hPTH and [Leu$^{25}$]hPTH, as well as analogues of these variants in which, for example, the methionines resident at one or both of positions 8 and 18 are replaced by an amino acid having a hydrophobic side chain, such as leucine;

(b) those in which the Lys$^{26}$ and Lys$^{27}$ residues are each replaced by a genetically encoded amino acid selected from histidine, tryptophan, glutamine, asparagine, leucine and isoleucine. Specific compounds of the present invention include [His$^{26}$His$^{27}$]hPTH, [His$^{26}$Leu$^{27}$]hPTH [His$^{26}$Asn$^{27}$]hPTH, [His$^{25}$Gln$^{27}$]hPTH, [His$^{26}$Trp$^{27}$]hPTH, [His$^{26}$Ile$^{27}$]hPTH, [Gln$^{26}$Gln$^{27}$]hPTH, [Asn$^{26}$Asn$^{27}$]hPTH and [Gln$^{26}$His$^{27}$]hPTH, as well as analogues of these variants in which, for example, the methionines resident at one or both of positions 8 and 18 are replaced by an amino acid having a hydrophobic side chain, such as leucine;

(c) those in which the Arg$^{25}$ residue and the LyS$^{26}$ residue are replaced by a genetically encoded amino acid selected from histidine, tryptophan, glutamine, asparagine, leucine and isoleucine. Specific compounds of the present invention include [His$^{25}$His$^{26}$]hPTH, [His$^{25}$Leu$^{26}$]hPTH, [His$^{25}$Asn$^{25}$]hPTH, [His$^{25}$Gln$^{26}$]hPTH, [His$^{25}$Trp$^{26}$]hPTH, [His$^{2-}$ 5Ile²⁶]hPTH, [Gln²⁵Gln²⁶]hPTH, [Asn²⁵Asn²⁶]hPTH and [Gln²⁵His²⁶]hPTH, as well as analogues of these variants in which, for example, the methionines resident at one or both of positions 8 and 18 are replaced by an amino acid having a hydrophobic side chain, such as leucine; and (d) those in which the Arg²⁵ residue and the Lys²⁷ residue are replaced by a genetically encoded amino acid selected from histidine, tryptophan, glutamine, asparagine, leucine and isoleucine. Specific compounds of the present invention include [His²⁵His²⁷]hPTH, [His²⁵Leu²⁷]hPTH, [His²⁵Asn²⁷]hPTH, [His²⁵Gln²⁷]hPTH, [His²⁵Trp²⁷]hPTH, [His²⁵Ile²⁷]hPTH, [Gln²⁵Gln²⁷]hPTH, [Asn²⁵Asn²⁷]hPTH and [Gln²⁵His²⁷]hPTH, as well as analogues of these variants in which, for example, the methionines resident at one or both of positions 8 and 18 are replaced by an amino acid having a hydrophobic side chain, such as leucine.

In a particularly preferred embodiment of the present invention, the PTH variants are variants of human PTH in which each of Arg²⁵, Lys²⁶ and Lys²⁷ is replaced by a genetically encoded amino acid selected from histidine, tryptophan, tyrosine, glutamine, asparagine, alanine, valine, leucine and isoleucine. It has been found that such human PTH variants are virtually resistant to trypsin digestion. It will be appreciated as well that such variants will also exhibit resistant to attack by enzymes other than trypsin which recognize basic residues, such as kallikrein and thrombin, and the kex enzymes which recognizes dibasic residues. Specific embodiments of the present invention include [His²⁵His²⁶Leu²⁷]hPTH, [His²⁵His²⁶His²⁷]hPTH, [His²⁵Leu²⁶Leu²⁷]hPTH, [His²⁵Gln²⁶His²⁷]hPTH, [His²⁵Asn²⁶His²⁷]hPTH, [His²⁵Trp²⁶His²⁷]hPTH, [His²⁵Gln²⁶Leu²⁷]hPTH, [His²⁵Leu²⁶His²⁷]hPTH, [His²⁵Ile²⁶His₂₇]hPTH, [Gln²⁵His²⁶His²⁷]hPTH and [Gln²⁵Gln²⁶His²⁷]hPTH, as well as analogues of these variants in which, for example, one or both methionines resident at positions 8 and 18 are replaced by an amino acid having a hydrophobic side chain, such as leucine.

As protein products, the PTH variants of the present invention are amenable to production by the technique of solution- or solid-phase peptide synthesis. The solid phase peptide synthesis technique, in particular, has been successfully applied in the production of human PTH and can be used for the production of the PTH variants of the present invention (for guidance, see Kimura et al, supra, and see Fairwell et al, Biochem., 1983, 22:2691). Success with producing human PTH on a relatively large scale has been reported by Goud et al in J. Bone Min. Res., 1991, 6(8):781, incorporated herein by reference. The synthetic peptide synthesis approach generally entails the use of automated synthesizers and appropriate resin as solid phase, to which is attached the C-terminal amino acid of the desired PTH variant. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, *Solid phase Peptide Synthesis*, 2nd Edition, 1984, Pierce Chemical Company, Rockford, Ill. It will be appreciated that the peptide synthesis approach is required for production of PTH variants which incorporate amino acids that are not genetically encoded.

In a preferred embodiment, the PTH variants of the present invention consist essentially of genetically encoded amino acids, and are produced in accordance with generally established recombinant DNA-based techniques of protein production. More particularly, and in accordance with one aspect of the present invention, such PTH variants are produced by culturing a cellular host in which DNA coding for the desired PTH variant is stably and expressibly incorporated. Incorporation of the desired DNA, in expressible form, can be achieved using established procedures, wherein DNA coding for the PTH variant is linked operably with DNA enabling expression of the PTH variant-encoding DNA, to form a recombinant DNA expression construct which is then introduced into the selected cellular host by DNA-mediated transformation, electroporation or the like. A cellular host having DNA coding for a PTH variant incorporated "expressibly" therein is characterized by the ability to yield the desired expression product, when cultured appropriately. A cellular host having DNA coding for a PTH variant incorporated "stably" is able to retain such DNA during culturing, and to transmit such DNA to its progeny through at least several generations. For eucaryotic cellular hosts, such stability is typically conferred by genomic integration of the PTH variant-encoding DNA. In bacteria, which typically harbour transforming DNA in the form of autonomously replicating plasmids, such stability is usually ensured by culturing a strain carrying plasmid-conferred antibotic resistance in the presence of the antibiotic.

For expression in the cellular host, DNA coding for a selected PTH variant may be obtained using techniques that are well established in the art. For example, a DNA sequence coding for a given PTH variant may be synthesized de novo in accordance with methods standard in the gene synthesis art. Briefly, this entails the successive 3' to 5' coupling of suitably protected nucleotide reagents in an automated DNA synthesizer, and then the recovery by gel purification of the deprotected polynucleotide. The block ligation approach may be employed, whereby "blocks" of oligonucleotide pairs, up to about 80 nucleotides in length, are prepared and ligated in correct succession by overhang complementarity to assemble the variant-encoding DNA, as described for example by Wosnick et al in Gene, 1989, 76:153. In an alternative approach, the desired DNA may be synthesized in toto, and then amplified by polymerase chain reaction (PCR), using the approach described by Barnett et al in Nucl. Acids Res., 1990, 18(10):3094.

It will be appreciated that alternative strategies may also be applied to generate DNA coding for the desired PTH variant. For instance, DNA coding for human PTH may be obtained and then used as a template e.g. mutagenized site-specifically, to introduce the desired amino acid change at the genetic level. DNA coding for human PTH may be obtained from an appropriate human cDNA library, from a commercial source or by de novo synthesis according to the procedures outlined above, and in accordance with the PTH-encoding nucleotide sequence reported for example by Hendy et al, Proc. Natl. Acad. Sci. USA, 1981, 78:7365, incorporated herein by reference, or a PTH-encoding equivalent thereof. The PTH-encoding DNA template may be converted to DNA coding for a PTH variant using the well established oligonucleotide-directed mutagenesis technique, as generally described for example by Kunkel et al, 1985, Proc. Natl. Acad. Sci. USA, 82:488. This technique is conveniently accomplished with high efficiency using the *E. coli*-based system for synthesis and propogation of the altered gene in an appropriate vector, such as M13mp18. Kits useful for performing such procedures in vitro are available commercially. Also suitable for obtaining PTH variant-encoding DNA from a PTH-encoding template is the related technique in which site-directed mutagenesis is achieved using a PCR-based approach. One variant of this method, termed "recombinant PCR" is described by Higuchi et al, Nucl. Acids. Res., 1988, 16:7351, and a modified "megaprimer" PCR approach is described in Biotechniques, 1990, 8(1):404.

Once obtained, DNA coding for the desired PTH variant is incorporated stably and expressibly into a cellular host selected to serve in production of the PTH variant. A variety of organisms are suitable as hosts for production of the PTH variants. These include eukaryotic hosts including yeasts such as Saccharomyces, Pichia and Kluveromyces, filamentous fungus hosts including Aspergillus species such as nidulans, niger (or awamori) and oryzae, insect cell hosts, and mammalian cell hosts including the CHO and COS cell lines. The PTH variants are not dependent on glycosylation for activity, and thus can suitably be produced in bacterial hosts including Streptomyces, Bacillus and, preferably, in *E. coli*. Recombinant DNA expression systems and culturing media/protocols enabling production in these hosts of a desired protein have already been established, and these systems may be employed in the conventional manner for the specific purpose of producing PTH variants. *E. coli* production of PTH variants may be achieved, for example, using expression systems based on the lac promoter (see Rabbani et al, Blochem., 1990, 29:10080) and expression/secretion systems based on the tac promoter (see Wong et al, EP 357,391 ). Yeast expression may be achieved using expression systems based for example on the expression controlling regions of the alpha-1 mating factor gene as described by Gautvik et al in WO88/03165. Production in Aspergillus may be achieved using secretion systems based on expression controlling regions of the A. nidulans alcA gene or the A. niger glucoamylase gene, as described for example by Gwynne et al in WO86/06097.

The PTH variant produced upon culturing of the production host is extracted and purified using techniques that are also established in the art. In general, the human PTH variants have characteristics that are similar generically to those exhibited by human PTH, and may therefore be extracted and purified in substantially the same manner. Like PTH, the variants have a net positive charge at neutral pH (pI of about 9.3) and can be purified therefore by ion exchange chromatography, e.g. using cation exchange columns. The PTH variants are also, like PTH, hydrophobic in nature, and may therefore be purified by hydrophobic interaction chromatography e.g. on columns having a phenyl-Sepharose matrix. Also, of course, molecular sieves may be used to separate PTH variants from other proteins unrelated by size, and affinity columns may be employed which comprise PTH affinity agents such as hydroxyapatite or PTH antibody. Preferably, purification of the PTH variant is achieved by applying the protein mixture to a cation exchange column e.g. S-Sepharose, and then applying the eluted retentate to a column having a hydrophobic matrix e.g. a column having a phenyl, octyl or butyl side chain such as phenyl-Sepharose, phenyl-Superose, octyl-Sepharose or butyl 650M. The retentate eluted from the hydrophobic matrix is then subjected to final purification using reversed phase high performance liquid chromatography (HPLC).

While the tryptic instability of human PTH typically demands that great care be taken during purification to guard against contamination by trypsin in glassware and during handling, extraction and purification of the PTH variants of the invention requires less stringent control measures. It is nevertheless desirable to exercise such control, in keeping with good laboratory and manufacturing practise.

For therapeutic use, a PTH variant is desirably purified to the extent that it migrates as a single peak on reversed phase HPLC, and exhibits a single band on polyacrylamide gel electrophoresis in the presence of SDS. Once purified, the PTH variant may be formulated to provide pharmaceutical compositions suitable for treating the various clinical conditions for which PTH therapy is indicated. Compositions containing PTH variant are administered desirably to treat bone disorders such as osteoporosis and other osteopenic conditions, and for these purposes are suitably formulated either as injectables or ingestibles or for nasal insufflation, in accordance with established practises of protein drug formulation. Sterile injectable compositions are particularly useful, and will generally comprise an effective dose of the PTH variant, in admixutre with normal saline and suitable solubilizing agent e.g. dilute acetic acid. The PTH variant may alternatively be applied topically, as a cream, lotion, ointment or as an aerosol, to treat psoriasis and related skin disorders. A suitable cream comprises an effective dose of the PTH variant, in combination with carriers of standard composition e.g. in a triglyceride base.

A therapeutically effective dose of PTH variant, i.e. a dose of PTH variant effective to treat a given clinical condition will depend of course on the nature and severity of the condition, and on such other factors as are normally considered and evaluated in clinical trials and by the attending physician. For treating osteoporosis, the PTH variant is administred in amounts large enough to stimulate bone remodelling, but not so large as to cause net bone resorption or sustained increase in serum calcium levels. Reference may be made to U.S. Pat. No. 4,698,328 for guidance on the administration of PTH to treat osteoporosis. Using the effective PTH doses in a given clinical situation for guidance, the dose of PTH variant required to elicit a similar effect can be calculated based on the relative activity of the PTH variant. For example, [His$^{25}$]hPTH, [His$^{25}$His$^{26}$Leu$^{27}$]hPTH and hPTH are substantially equipotent, and effective doses of these PTH variants are thus similar to those of hPTH. It is expected that the improved stability in the presence of trypsin of the PTH variants will provide for extended in vivo half-life, and thus somewhat smaller doses may be used or simular doses may be administered less frequently. It is anticipated that dosage sizes in the range from 0.05 μg/kg to about 1,000 μg/kg, for example in the range from 0.1 μg/kg to 100 μg/kg, and more suitably about 1–10 μg/kg will be clinically useful.

Like PTH, the PTH variants may be administered in combination with other agents useful in treating a given clinical condition. When treating osteoporosis and other bone-related disorders for example, the PTH variants may be administered in conjunction with a dietary calcium supplement or with a vitamin D analogue (see U.S. Pat. No. 4,698,328). Alternatively, the PTH variant may be administered, preferably using a cyclic therapeutic regimen, in combination with bisphosphonates, as described for example in U.S. Pat. No. 4,761,406, or in combination with one or more bone therapeutic agents such as calcitonin and estrogen.

EXAMPLES

The examples which follow describe production of human PTH and human PTH variants. Production of these proteins was achieved using, as a matter of convenience only, an *E. coli*-based system substantially as described by Wong ant Sutherland in European patent application 89308753.6 (published as EP357,391 on 7 March 1990), the contents of which are incorporated herein by reference. This system makes use of the commonly available *E. coli* JM101 strain as host and employs as vector a pUC18 derivative, designated pX. As is shown in FIG. 1, pX incorporates the par element of pSC101 to enhance frequency of plasmid transmission, the laclq gene of pMMB22 to enable overproduction of the lac repressor, and a PTH-excretion cassette. Incorporated in the excretion cassette is human PTH-encoding DNA that was synthesized using the block ligation technique reported by Wosnick et al, supra, and in accordance with the PTH-encoding nucleotide sequence reported by Hendy et al, supra. Fused 5' of, and precisely to, the PTH-encoding DNA is the signal sequence of the *E. coli* ompA gene, which is capable of directing the PTH portion of the expression product across the host inner membrane, and ultimately to the culturing medium. For regulated expression of the coding region, the plasmid operably incorporates the tac promoter, the lac operator and a consensus ribosomal binding site. Transcriptional termination is controlled by the *E. coli* trpA gene terminator, and translational stop codons are provided in all three reading frames, immediately 3' of the PTH-encoding DNA.

Thus, the pX expression vector, used for the production of human PTH and PTH variants, is substantially the same as that described by Wong and Sutherland, supra, except that the multiple cloning site downstream of the PTH gene contains cleavage sites for the restriction enzymes ClaI, BamHI, XbaI, StuI and PstI, in the order indicated on FIG. 1. The precise nucleotide sequence of the PTH-encoding region of the excretion cassette is illustrated in FIG. 2.

Example 1—Production of human PTH(1-84)

Plasmid pX was transformed into competent *E. coli* JM1 01 using standard procedures. Positive transformants were indentified following growth overnight at 30° C., on plates containing 2YT/agar and 70µg/ml ampicillin. PTH-producing transformants were then examined for PTH activity, following growth in shake flasks, by IRMA analysis of conditioned medium, and frozen stocks of the selected transformants were subsequently prepared by mixing an equal volume of the shake flask culture with sterile glycerol to yield 50%(v/v) glycerol stocks. These stocks were subsequently stored at −80° C. When needed, transformants were recovered from the frozen stock by scraping, and were then streaked on ampicillin-containing plates of 2YT/agar.

To produce human PTH, freshly plated transformants were picked as single colonies and then inoculated into 50ml Erlenmeyer flasks containing 15 ml of a liquid medium which contained 2YT, glucose and ampicillin in the standard mixture. Following overnight growth with shaking at 30° C., the cultures were diluted 20-fold with fresh medium, and then grown for three hours at 30° C. with shaking. Expression of the PTH-encoding DNA was then de-repressed by addition of 1.0 mM IPTG. After growth for four hours in the presence of IPTG, the culture was cooled to 4° C. and centrifuged. The supernatant was then harvested and human PTH contained therein was recovered and assayed for PTH activity.

To obtain sufficient quantities of human PTH(1-84) and the PTH variants for purification and bioassay, larger volumes of conditioned media were collected. In particular, freshly plated transformants were picked as single colonies and then inoculated into 500 ml flasks containing 200 ml of the medium described above. Following overnight growth with shaking at 30° C., the cultures were inoculated into 2L bioreactors containing 1.5L of the liquid medium, and then grown for 5 hours at 30° C. with stirring. Expression of the PTH- or PTH variant-encoding DNA was then induced by addition of 1.0 mM IPTG. After growth for 3-4 hours in the presence of IPTG, the culture was cooled to 4° C. and centrifuged. The supernatant was then harvested, and the PTH or PTH variant contained therein was purified in the manner described in Example 5.

The examples which follow describe production of PTH variants. To obtain DNA coding for these variants, the in vitro site-directed mutagenesis technique described by Kunkel et al, supra, was applied. To perform this procedure there was first obtained plasmid RX which is an M13 mp18-based version of the excretion cassette on pX, carrying the PTH-encoding DNA as a promoterless NruI/XbaI insert. Plasmid RX thus served as the template for conducting mutagenesis on the PTH-encoding DNA, in order to generate DNA coding for a desired PTH variant. The particular mutagenesis strategy is described in the examples below.

Example 2—Production of a [His$^{25}$] variant of PTH

To provide DNA coding for a PTH variant in which Arg$^{25}$ is replaced by histidine, plasmid RX was first recovered in single stranded form and about 1 µg thereof was incubated, at 85° C. in Hin buffer, with about 100 ng of a mutagenic oligonucleotide capable of hybridizing specifically to that region of the PTH gene containing the Arg$^{25}$ codon. The specific sequence of the oligonucleotide, designated P1, is shown below where underlining indicates the codon change relative to the PTH-encoding template shown in FIG. 2:

P1 oligo (SEQ ID NO: 3):     5' CAGCTTCTT<u>GTG</u>CAGCCATTCTAC 3'
template (SEQ ID NO: 4): 3' ... GTCGAAGAATGCGTCGGTAAGATG ... 5'

After slow cooling, the annealed fragment was treated with DNA polymerase I (Klenow) in the presence of all four dNTPs, for about 2 hours at 37° C. and then for 4 hours at room temperature, in order to form the full length double-stranded plasmid, designated pRXP1. Competent host JM101 was then transformed by pRXP1, and plaques were screened by restriction digest analysis and by DNA sequencing to select those carrying the desired mutation.

pRXP1 is then digested with NruI and XbaI and the resulting small fragment is isolated by low melting point agarose. Plasmid pX is similarly digested, and the large NruI/XbaI fragment is isolated. The relevant isolated fragments are then ligated, to form plasmid pXP1, which carries DNA coding for [His$^{25}$]hPTH. This was confirmed by restriction digest analysis and DNA sequencing.

Competent E. coli JM101 was transformed with pXP1 and the transformants were then selected in accordance with the procedures outlined in Example 1. Supernatant containing the [His$^{25}$]PTH was then obtained for subsequent purification by culturing the pXP1 transformant, in the manner described by example 1.

Example 3—Production of a [His$^{25}$His$^{26}$Leu$^{27}$]variant of PTH

In a manner similar to that described in Example 2, there was obtained DNA coding for a human PTH variant in which the native sequence Arg$^{25}$Lys$^{26}$Lys$^{27}$ is replaced by the sequence His$^{25}$His$^{26}$Leu$^{27}$. In particular, single stranded pRX was incubated with an oligonucleotide having the sequence provided below, where underlining indicates the codon change relative to the native PTH-encoding template shown in FIG. 2:

P2 oligo (SEQ ID NO: 5)      5' CATCCTGCAG<u>CAGGTGGTGC</u>AGCCATTCTACTCT 3'
PTH template (SEQ ID NO: 6) 3'... GTAGGACGTCGAAGAATGCGTCGGTAAGATGAGA ... 5'

A double stranded plasmid carrying the desired codon replacements, designated pRXP2, is then cut with NruI/XbaI and the isolated small fragment is ligated with the large fragment of NruI/XbaI-digested pX. E. coli was then transformed by the resulting plasmid pXP2, and the transformant was cultured in the manner outlined in Example 1 to yield supernatant containing [His$^{25}$His$^{26}$Leu$^{27}$]hPTH.

Example 4—Production of additional PTH variants

In the manner substantially as described above in example 3, supernatants containing additional PTH variants are obtained by culturing E. coli transformants habouring PTH variant-encoding DNA. To generate the variant-encoding DNA, DNA coding for native hPTH (Example 2)is used as template and is incubated with a mutagenic oligonucleotide having the sequence noted below. For convenience herein, the annealing flanks of each oligonucleotide are not represented. Rather, the sequence of the mutagenic oligonucleotide in the Arg$^{25}$Lys$^{26}$Lys$^{27}$ region is represented and the codon alteration is identified by underlining. The resulting amino acid change is also identified:

```
                                           27  26  25
PTH amino acids                         ... Lys Lys Arg ...
PTH template (SEQ ID NO: 7)  3' ... GTAGGACGTCGAAGAATGCGTCGGTAAGATGAGA ... 5'
oligo sequence (SEQ ID NO: 8) 5' ... CATCCTGCAG[   -below-   ]CAGCCATTCTACTCT ... 3'
```

[Gln$^{25}$] from —CTTCTT<u>CTG</u>—; [Asn$^{25}$] from —CTTCTT<u>GTT</u>—; [Trp$^{25}$] from —CTTCTT<u>CCA</u>—

[Leu$^{25}$] from —CTTCTT<u>CAG</u>—; [Ile$^{25}$] from —CTTCTT<u>GAT</u>—;[Ala25] from —CTTCTT<u>AGC</u>—;

[Val25] from —CTTCTT<u>AAC</u>—; [Pro25] from —CTTCTT<u>CGG</u>—;[Phe25] from —CTTCTT<u>GAA</u>—

[Tyr25] from —CTTCTT<u>GTA</u>—; [Ser25] from —CTTCTT<u>GGA</u>—; [Thr25] from —CTTCTT<u>GGT</u>—

[His$^{25}$His$^{26}$] from —CTT<u>GTGGTG</u>—; [His$^{25}$Gln$^{26}$] from —CTT<u>CTGGTG</u>—

[His$^{25}$Asn$^{26}$] from —CTT<u>GTTGTG</u>—; [His$^{25}$Trp$^{26}$] from —CTT<u>CCAGTG</u>—

[His$^{25}$Leu$^{26}$] from —CTT<u>CAGGTG</u>—; [His$^{25}$Ile$^{26}$] from —CTT<u>GATGTG</u>—

[Gln$^{25}$Gln$^{26}$] from —CTT<u>CTGCTG</u>—; [Asn$^{25}$Asn$^{26}$] from —CTT<u>GTTGTT</u>—;

[Gln$^{25}$His$^{26}$] from —CTT<u>GTGCTG</u>—; [His$^{25}$Ala$^{26}$] from —CTT<u>AGCGTG</u>—

[His$^{25}$Val$^{26}$] from —CTT<u>AACGTG</u>—; [His$^{25}$Pro$^{26}$] from —CTT<u>CGGGTG</u>—

[Gln$^{25}$Asn$^{26}$] from —CTT<u>GTTCTG</u>—; [Gln$^{25}$Ala$^{26}$] from —CTT<u>AGCCTG</u>—

[Gln$^{25}$Val$^{26}$] from —CTT<u>AACCTG</u>—; [Gln$^{25}$Leu$^{26}$] from —CTT<u>CAGCTG</u>—

[Gln$^{25}$Ile$^{26}$] from —CTT<u>GATCTG</u>—; [Gln$^{25}$Pro$^{26}$] from —CTT<u>CGGCTG</u>—

[Asn$^{25}$His$^{26}$] from —CTT<u>CTGGTT</u>—; [Asn$^{25}$Gln$^{26}$] from —CTT<u>CTGGTT</u>—

[Asn$^{25}$Ala$^{26}$] from —CTT<u>AGCGTT</u>—; [Asn$^{25}$Val$^{26}$] from —CTT<u>AACGTT</u>—

[Asn$^{25}$Leu$^{26}$] from —CTT<u>CAGGTT</u>—; [Asn$^{25}$Ile$^{26}$] from —CTT<u>GATGTT</u>—

[Asn$^{25}$Pro$^{26}$] from —CTT<u>CGGGTT</u>—.

[His25His27] from —<u>GTG</u>CTT<u>GTG</u>—;[His25Leu27] from —<u>CAG</u>CTT<u>GTG</u>—;

[His25Asn27] from —<u>GTT</u>CTT<u>GTG</u>—;[His25Gln27] from —<u>CTG</u>CTT<u>GTG</u>—;

[His25Trp27] from —<u>CCA</u>CTT<u>GTG</u>—;[His25Ile27] from —<u>GAT</u>CTT<u>GTG</u>—;

[His25Ala27] from —<u>AGC</u>CTT<u>GTG</u>—;[His25Val27] from —<u>AAC</u>CTT<u>GTG</u>—;

[His25Pro27] from —<u>CGG</u>CTT<u>GTG</u>—;[Gln25His27] from —<u>GTG</u>CTT<u>CTG</u>—;

[Gln25Leu27] from —<u>CAG</u>CTT<u>CTG</u>—;[Gln25Asn27] from —<u>GTT</u>CTT<u>CTG</u>—;

[Gln25Gln27] from —<u>CTG</u>CTT<u>CTG</u>—;[Gln25Trp27] from —<u>CCA</u>CTT<u>CTG</u>—;

-continued

[Gln25Ile27] from —GATCTTCTG—;[Gln25Ala27] from —AGCCTTCTG—;
[Gln25Val27] from —AACCTTCTG—;[Gln25Pro27] from —CGGCTTCTG—;
[Asn25His27] from —GTGCTTGTT—;[Asn25Leu27] from —CAGCTTGTT—;
[Asn25Asn27] from —GTTCTTGTT—;[Asn25Gln27] from —CTGCTTGTT—;
[Asn25Trp27] from —CCACTTGTT—;[Asn25Ile27] from —GATCTTGTT—;
[Asn25Ala27] from —AGCCTTGTT—;[Asn25Val27] from —AACCTTGTT—;
[Asn25Pro27] from —CGGCTTGTT—.

[His26His27] from —GTGGTGACG—;[His26Leu27] from —CAGGTGACG—;
[His26Asn27] from —GTTGTGACG—;[His26Gln27] from —CTGGTGACG—;
[His26Trp27] from —CCAGTGACG—;[His26Ile27] from —GATGTGACG—;
[His26Ala27] from —AGCGTGACG—;[His26Val27] from —AACGTGACG—;
[His26Pro27] from —CGGGTGACG—;[Gln26His27] from —GTGCTGACG—;
[Gln26Leu27] from —CAGCTGACG—;[Gln26Asn27] from —GTTCTGACG—;
[Gln26Gln27] from —CTGCTGACG—;[Gln26Trp27] from —CCACTGACG—;
[Gln26Ile27] from —GATCTGACG—;[Gln26Ala27] from —AGCCTGACG—;
[Gln26Val27] from —AACCTGACG—;[Gln26Pro27] from —CGGCTGACG—;
[Asn26His27] from —GTGGTTACG—;[Asn26Leu27] from —CAGGTTACG—;
[Asn26Asn27] from —GTTGTTACG—;[Asn26Gln27] from —CTGGTTACG—;
[Asn26Trp27] from —CCAGTTACG—;[Asn26Ile27] from —GATGTTACG—;
[Asn26Ala27] from —AGCGTTACG—;[Asn26Val27] from —AACGTTACG—;
[Asn26Pro27] from —CGGGTTACG—.

[His$^{25}$His$^{26}$His$^{27}$] from —GTGGTGGTG—;[His$^{25}$Gln$^{26}$His$^{27}$] from —GTGCTGGTG—;
[His$^{25}$Asn$^{26}$His$^{27}$] from —GTGGTTGTG—;[His$^{25}$Trp$^{26}$His$^{27}$] from —GTGCCAGTG—;
[His$^{25}$Leu$^{26}$His$^{27}$] from —GTGCAGGTG—;[His$^{25}$Ile$^{26}$His$^{27}$] from —GTGGATGTG—;
[His25Leu26Leu27] from —CAGCAGGTG—;[His25Gln26Leu27] from —CAGCTGGTG—;
[Gln25His26His27] from —GTGGTGCTG—;[Gln25Gln26His27] from —GTGCTGCTG—.

Analogues of the PTH variants of the invention can be generated in substantially the same manner, but using template DNA that codes for an analogue of PTH. To generate an analogue that incorporates replacement of methionine by leucine at position 8, for example, a template coding for [Leu$^8$]hPTH is obtained using the site-directed mutagenesis technique as described in co-pending application U.S. Ser. No. 07/806,271 filed Dec. 13, 1991 and incorporated herein by reference, and the [Leu$^8$]hPTH-encoding DNA is then used as template for a second round of site-directed mutagenesis in which an oligonucleotide capable of introducing a desired codon change in the Arg$^{25}$Lys$^{26}$Lys$^{27}$ region is utilized.

Example 5—Purification and Evaluation of PTH and PTH variants

The conditioned medium collected from the transformants of Examples 1-3 was, in each case, adjusted to about pH 4 with glacial acetic acid, and the solution was centrifuged. The supernatant was harvested and then passed through a column containing the cation exchange resin S-Sepharose FastFlow (Pharmacia, bed volume 50 ml) pre-equilibrated with 0.04M ammonium acetate/10 mM B-mercaptoethanol (pH4.0). Resin-bound PTH or PTH variant was eluted by applying a concentration gradient of ammonium acetate as eluant of from 0.04M-1.0M ammonium acetate/10 mM B-mercaptoethanol (pH4.0). PTH or the PTH variant eluted from the resin at about 0.6M ammonium acetate. Eluant fractions, containing PTH or the PTH variant (as measured by the Allegro two-site IRMA purchased form Joldan Diagnostics, California, catalogue #40-2170, or by absorbance at 280 nm), were combined to provide PTH or variant at about 60-70% purity.

Samples of greater purity were obtained by subjecting the combined fractions to a chromatographic separation using the resin phenyl-Sepharose FastFlow (Pharmacia). More particularly, the pH of the combined S-Sepharose fractions was adjusted to pH 8 with 5N NaOH. This solution was then applied to a column containing phenyl-Sepharose (6 ml bed volume), pre-equilibrated with the buffer (6 volumes of 1.0M ammonium acetate (pH4.0) and 4 volumes of 40 mM ammonium acetate (pH4.0), then adjusted to pH 8.0 with 5N NaOH. PTH or variant adsorbed to the column was then eluted using as eluant a concentration gradient of buffer to 0.6M ammonium acetate (pH8.0).

Fractions containing PTH activity (as measured by Allegro two-site IRMA or monitored by $A_{280}$) were combined and then desalted by passage through a cartridge containing reversed phase C-18 resin e.g. Sep-Pak (Waters Inc.) or Amberchrom CG71 resin (Toso Haas) pre-equilibrated with 0.1% TFA. The PTH or variant bound to the resin was eluted with 0.1% TFA/80% acetonitrile and desalted preparations were then frozen in liquid nitrogen, lyophilized and stored at −20° C.

Thawed or fresh samples of human PTH(1-84) and of PTH variants obtained as described above were then evaluated for biological activity using a UMR-106 based adenylate cyclase assay and the protocol as described by Rabbini et al, 1988, Endocrinology, 123:2709, which is incorporated herein by reference. As noted, rat osteosarcoma cells of the UMR line are stimulated by PTH to produce adenylate cyclase, an enzyme which catalyzes intracellular conversion of ATP to its cylic monophosphate analogue, cAMP. In this assay therefore, PTH activity is determined by assaying radiometrically the formation of cAMP in PTH-stimulated UMR cells. The results of the assays, expressed in terms of $EC_{50}$ (concentration of PTH or variant effective for half-maximal stimulation of adenylate cyclase activity), are presented in the table below:

Table 1: Concentration of PTH and Variants Effective for Half-maximal Stimulation of Adenylate Cyclase Activity

TABLE 1

| Concentration of PTH and Variants Effective for Half-Maximal Stimulation of Adenylate Cyclase Activity | |
|---|---|
| Compound | $EC_{50}$ (nM) |
| hPTH | 1.0 |
| [His$^{25}$]hPTH | 2.0 |
| [His$^{25}$His$^{26}$Leu$^{27}$]hPTH | 1.7 |

It is evident from the results presented in Table 1 that PTH variants altered in the trypsin-sensitive region are substantially equipotent with human PTH. The effect of amino acid replacement in this region on sensitivity to trypsin was next evaluated by comparing trypsin effects on PTH variants relative to a human PTH control, in the following manner.

To measure the sensitivity of a compound (native PTH or variants) to digestion with trypsin, duplicate incubations were established for each compound in either the presence of trypsin ("Trypsin Incubation") or the absence of trypsin ("Mock Incubation"). For example, a lyophilized aliquot of PTH (or variant) was solubilized for 20 minutes at room temperature in 10 mM acetic acid at a final concentration of 1 mg/mL (50 μg PTH or variant plus 50 μL 10 mM acetic acid). Following complete solubilization in acetic acid, the sample was diluted with buffer (50 mM Tris. HCl pH 7.5, "Tris buffer", to a final concentration of 1 μg/20.82 μL). A fresh trypsin stock solution was prepared for each experiment by solubilizing trypsin in Tris buffer to a final concentration of 10 μg/mL (20 μg trypsin plus 2 mL Tris buffer). The activity of the trypsin stock solution was established spectrophometrically at the beginning and the end of each experiment by monitoring its ability to cleave the synthetic substrate N-α-benzoyl-L-arginine ethyl ether (BAEE). The appearance of the cleavage product was monitored as a function of time at 253 nm. A fresh stock solution of soybean trypsin inhibitor (SBTI) was prepared in Tris buffer at a final concentration of 10 μg/mL. The ability of the SBTI stock solution to quench the activity of the trypsin stock solution was verified by the addition of an equal weight of SBTI to trypsin in the trypsin/BAEE mixture (i.e. 5 μg trypsin in trypsin/BAEE solution plus 5 μg SBTI solution).

Parallel trypsin and mock incubations were established as follows. Identical amounts of the PTH or variant sample in Tris buffer were added to each of two tubes (416.4 μL of PTH or variant sample in Tris buffer at 1 μg/20.82 μL for a total of 20 μg of PTH or variant in each of two tubes). The trypsin incubation received an amount of trypsin stock solution in Tris buffer so that the final weight of trypsin to PTH (or variant) was 1:500 (w:w) (e.g. 0.4 μg of trypsin was added to 20 μg of PTH or variant or 4 μL of trypsin stock solution containing 10 82 g/mL was added to 416.2 μL of PTH or variant solution containing 1 μg/20.82 μL). The mock incubation received Tris buffer alone lacking trypsin in an amount equal to the volume of trypsin used for the parallel incubation (e.g. 4 μL of Tris buffer added to 416.2 μL of PTH or variant solution containing 1 μg/20.82 μL). The parallel tubes were then incubated for 4 hours at room temperature and were then "quenched" by the addition of an amount of SBTI sufficient to inhibit completely the trypsin (4 μL of SBTI solution in Tris buffer at a concentration of 10 μg SBTI/mL was added to each tube). A portion of each of the incubation mixtures was used to construct a series of dilutions of PTH (or variant) to test in the UMR-106 cell adenylate cyclase assay. Particularly, the quenched incubations were diluted appropriately with assay buffer to a final concentration of $5 \times 10^{-7}$ M (200 μL of quenched sample described above containing PTH or variant at $5 \times 10^{-6}$ M was diluted 10-fold with 1800 μL assay buffer). Appropriate serial dilutions (from $5 \times 10^{-7}$ M to $3 \times 10^{-11}$ M) were made with assay buffer for the trypsin incubation samples and for the mock incubation samples. Dose-response curves were generated and the relevant $EC_{50}$ values were calculated. $EC_{50}^{trypsin}$ and $EC_{50}^{mock}$ correspond to the $EC_{50}$ values for the trypsin and mock incubations, respectively. The trypsin sensitivity (TS) for PTH (or a variant) was calculated as the ratio of $EC_{50}^{trypsin}/EC_{50}^{mock}$ for the sample. The loss in bioactivity as a result of trypsin digestion at one or more lysine or arginine residues in the N-terminal portion of PTH (e.g. Lys$^{13}$, Arg$^{25}$, Arg$^{25}$,Lys$^{26}$, Lys$^{27}$) will result in an increase in $EC_{50}$ mock and thus a TS value that is greater than one. The average TS values (5 experiments) for PTH and two variants are summarized in Table 2. The relative resistance (RR) of a variant compared to native PTH was calculated as the ratio of the trypsin sensitivity of PTH to that of the analogue (i.e. $RR^{variant} = TS^{native}/TS^{variant}$). The greater the RR value, the more resistant the bioactivity of the variant is to trypsin degradation.

TABLE 2

| Retention of Biological Activity of PTH and Variants Following Incubation with Trypsin | | |
|---|---|---|
| Compound | Trypsin Sensitivity (TS) | Relative Resistance (RR) |
| hPTH (1-84) | 12 ± 4 | 1.0 |
| [R25H] | 7 ± 3 | 2.1 ± 0.9 |
| [R25H/K26H/K27L] | 2.4 ± 0.5 | 5.1 ± 0.7 |
| TS = $EC_{50}^{trypsin}/EC_{50}^{mock}$ | | |
| RR = $TS^{native}/TS^{variant}$ | | |

The stability of PTH and variants to degradation by trypsin was also quantified by SDS polyacrylamide gel electrophoresis (SDS-PAGE). Incubations of PTH or variant with trypsin were established. For example, a sufficient aliquot of lyophilized PTH or variant was first solubilized for 20 minutes at room temperature with 10 mM acetic acid (final concentration of 1 mg/mL) and then diluted about 20-fold with Tris buffer. About 10 μg of PTH (or variant) was removed for a preincubation, "time zero" time point, and was lyophilized. The incubations were initiated by addition of an appropriate amount of freshly prepared trypsin solution in Tris buffer for a final trypsin to PTH (or variant) ratio of 1:500 (w/w). The samples were incubated at room temperature. Aliquots of the appropriate volume corresponding to an initial amount of undigested PTH (or variant) of 10 μg were removed at specific times (2, 5, 20, 60, 240 minutes). These were quenched immediately by adding an equal weight of SBTI to trypsin (either 2 μL of SBTI in Tris at a concentration of 10 μg/mL or 0.02 μg SBTI was added to the time point containing 0.02 μg trypsin and 10 μg initial equivalent amount of PTH or variant in Tris buffer). Samples quenched at the various time points were then lyophilized.

Analyses of the lyophilized preincubation sample and the lyophilized time point samples were carried out using SDS-PAGE methods such as those described by Laemmli, 1970,Nature (London) 227:680–685. An improved SDS-PAGE system for the analysis of samples such as intact and fragmented PTH with low to moderate amounts of salt is described by Schagger and von Jagow (1987) Analytical Biochemistry 166:368–379 and was used for the analysis of the trypsin digestion time course studies. Lyophilized samples containing 10 μg of intact and/or fragmented PTH or variant were solubilized in gel sample buffer and subjected to electrophoresis using suitable conditions to separate intact PTH from the smaller fragments (16.5% acrylamide gel, BioRad Mini-Protean II apparatus, 90 minutes, 100 mV). The gels were fixed and stained for protein with Coomassie Blue. The amount of intact, full length PTH present in each of the various samples (preincubation sample and time point samples) was quantified using a gel scanning method, which measures the quantity of stain and therefore the amount of protein scanned in each band. Initially, a standard curve was constructed by loading various amounts of PTH in each lane (2,2, 4, 6, 8, 10 μg per lane), scanning each lane, and then constructing a standard curve of the quantity of stain at the mobility of PTH as a function of the amount of PTH loaded per lane. With the gel scanning system, the quantity of stain was proportional to the amount of PTH loaded in the range of 1 to 10 μg per lane. Using this standard curve, the amount of intact PTH present in each sample was calculated from the quantity of stain at the mobility of intact PTH.

The amount of PTH (or variant) in the preincubation sample was termed $P_o$ (scanned amount corresponding to approximately 10 μg intact PTH or variant) and the amount at a given time, t, was defined as $P_t$. A plot of $P_t/P_o$ versus time (t) for PTH showed the time-dependent loss in intact PTH upon incubation with trypsin. At a trypsin to PTH ratio of 1:500 (w/w) the [His25His26Leu27]variant was almost completely resistant to proteolysis (see Table 3). After 240 minutes, more than 60% of the initial material remained. Under these conditions, the other Arg and Lys sites in the [His25His26Leu27] variant are not very susceptible to trypsin digestion. The half-life of PTH (or variant) under these conditions of trypsin degradation was measured from plots of $P_t/P_o$ versus time (t) as the time when 50% of the intact PTH (or variant) had been at least partially degraded (i.e. $P_t/P_o=0.5$).

TABLE 3

| Stability of PTH and Variants to Trypsin Degradation | |
|---|---|
| Compound | Half-Life (from SDS-PAGE analysis) Trypsin:PTH = 1:500 (w/w) |
| hPTH (1-84) | 25 ± 5 min. |
| [R25H] | 27 ± 7 min. |
| [R25H/K26H/K27L] | >>240 min. |

Example 6—In vivo efficacy study

The P2 variant was also evaluated in vivo for its effect on skeletal tissue, in an ovariectomized rat model of osteoporosis. Formulations of the P2 variants were first prepared by reconstituting the P2 variant from lyophilized powder in 0.1M acetic acid, then diluting to 10 mM acetic acid by addition of normal saline vehicle and 2% (v/v) heat-inactivated rat serum, to generate a stock solution containing the variant at a concentration of about 150 μg/ml. The P2 formulation was then injected subcutaneously at the neck region, in selected volumes representing dosage sizes of 25 μg/kg and 150 μg/kg (8 rats/each dose). A third group of rats received human PTH at a dose of 150 μg/kg and a fourth group received vehicle alone. Treatment regimen consisted of single dose administration once daily for 28 days.

After treatment, the rats were sacrificed and evaluated by total skeletal calcium scan. Relative to rats receiving vehicle alone, the whole body calcium scanning results indicated an improvement in rats receiving human PTH (5.8% increase), and a still further improvement (9.6% increase) in rats receiving the [His2-5His26Leu27] variant. It is believed that enhanced effects of this variant result from its greater half-life in vivo i.e. its resistant to serum-borne trypsin and/or other enzymes which otherwise degrade and/or inactivate the native hormone.

We claim:

1. A stability-enhanced variant of a nature parathyroid hormone that has a region of Arg$^{25}$ Lys$^{26}$ Lys$^{27}$ wherein said variant has Arg$^{25}$ replaced by His$^{25}$.

2. A stability-enhanced variant of a nature parathyroid hormone that has a region of Arg$^{25}$ Lys$^{26}$ Lys$^{27}$ wherein said variant has Arg$^{25}$ Lys$^{26}$ Lys$^{27}$ replaced by His$^{25}$ His$^{26}$ Leu$^{27}$.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( i x ) FEATURE:
        ( A ) NAME/KEY: CDS
        ( B ) LOCATION: 1..252

( D ) OTHER INFORMATION: /product="hPTH"

( x i ) SEQUENCE DESCRIPTION: SEQ ID NO:1:

| TCT | GTG | AGT | GAA | ATA | CAG | CTT | ATG | CAT | AAC | CTG | GGA | AAA | CAT | CTG | AAC | 48 |
| Ser | Val | Ser | Glu | Ile | Gln | Leu | Met | His | Asn | Leu | Gly | Lys | His | Leu | Asn | |
| 1 | | | | 5 | | | | | 10 | | | | | 15 | | |

| TCG | ATG | GAG | AGA | GTA | GAA | TGG | CTG | CGT | AAG | AAG | CTG | CAG | GAT | GTG | CAC | 96 |
| Ser | Met | Glu | Arg | Val | Glu | Trp | Leu | Arg | Lys | Lys | Leu | Gln | Asp | Val | His | |
| | | | 20 | | | | | 25 | | | | | 30 | | | |

| AAT | TTT | GTT | GCC | CTT | GGA | GCT | CCT | CTA | GCT | CCC | AGA | GAT | GCT | GGT | TCC | 144 |
| Asn | Phe | Val | Ala | Leu | Gly | Ala | Pro | Leu | Ala | Pro | Arg | Asp | Ala | Gly | Ser | |
| | | 35 | | | | | 40 | | | | | 45 | | | | |

| CAG | AGG | CCC | CGA | AAA | AAG | GAA | GAC | AAT | GTC | TTG | GTT | GAG | AGC | CAT | GAA | 192 |
| Gln | Arg | Pro | Arg | Lys | Lys | Glu | Asp | Asn | Val | Leu | Val | Glu | Ser | His | Glu | |
| | 50 | | | | | 55 | | | | | 60 | | | | | |

| AAA | AGT | CTT | GGA | GAG | GCA | GAC | AAA | GCT | GAT | GTG | AAT | GTA | TTA | ACT | AAA | 240 |
| Lys | Ser | Leu | Gly | Glu | Ala | Asp | Lys | Ala | Asp | Val | Asn | Val | Leu | Thr | Lys | |
| 65 | | | | 70 | | | | | 75 | | | | | 80 | | |

| GCT | AAA | TCC | CAG | | | | | | | | | | | | | 252 |
| Ala | Lys | Ser | Gln | | | | | | | | | | | | | |

( 2 ) INFORMATION FOR SEQ ID NO:2:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ser | Val | Ser | Glu | Ile | Gln | Leu | Met | His | Asn | Leu | Gly | Lys | His | Leu | Asn |
| 1 | | | | 5 | | | | | 10 | | | | | 15 | |

| Ser | Met | Glu | Arg | Val | Glu | Trp | Leu | Arg | Lys | Lys | Leu | Gln | Asp | Val | His |
| | | | 20 | | | | | 25 | | | | | 30 | | |

| Asn | Phe | Val | Ala | Leu | Gly | Ala | Pro | Leu | Ala | Pro | Arg | Asp | Ala | Gly | Ser |
| | | 35 | | | | | 40 | | | | | 45 | | | |

| Gln | Arg | Pro | Arg | Lys | Lys | Glu | Asp | Asn | Val | Leu | Val | Glu | Ser | His | Glu |
| | 50 | | | | | 55 | | | | | 60 | | | | |

| Lys | Ser | Leu | Gly | Glu | Ala | Asp | Lys | Ala | Asp | Val | Asn | Val | Leu | Thr | Lys |
| 65 | | | | 70 | | | | | 75 | | | | | 80 | |

| Ala | Lys | Ser | Gln |

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:3:

CAGCTTCTTG TGCAGCCATT CTAC        24

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid;

(A) DESCRIPTION: Synthetic DNA oligonucleotide (xi) SEQUENCE DESCRIPTION: SEQ ID NO:4:

GTCGAAGAAT GCGTCGGTAA GATG                                    24

(2) INFORMATION FOR SEQ ID NO:5:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (xi) SEQUENCE DESCRIPTION: SEQ ID NO:5:

CATCCTGCAG CAGGTGGTGC AGCCATTCTA CTCT                         34

(2) INFORMATION FOR SEQ ID NO:6:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (xi) SEQUENCE DESCRIPTION: SEQ ID NO:6:

GTAGGACGTC GAAGAATGCG TCGGTAAGAT GAGA                         34

(2) INFORMATION FOR SEQ ID NO:7:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (xi) SEQUENCE DESCRIPTION: SEQ ID NO:7:

GTAGGACGTC GAAGAATGCG TCGGTAAGAT GAGA                         34

(2) INFORMATION FOR SEQ ID NO:8:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (xi) SEQUENCE DESCRIPTION: SEQ ID NO:8:

CATCCTGCAG NNNNNNNNNC AGCCATTCTA CTCT                         34